(12) United States Patent
Tran

(10) Patent No.: US 7,300,464 B2
(45) Date of Patent: Nov. 27, 2007

(54) INTRAOCULAR LENS

(75) Inventor: Son Trung Tran, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 427 days.

(21) Appl. No.: 10/955,111

(22) Filed: Sep. 30, 2004

(65) Prior Publication Data

US 2006/0069432 A1 Mar. 30, 2006

(51) Int. Cl.
*A61F 2/16* (2006.01)

(52) U.S. Cl. .................................. 623/6.41

(58) Field of Classification Search ........... 623/6.11, 623/6.15, 6.17, 6.34, 6.38, 6.4, 6.41, 6.43, 623/6.6, 4.1
See application file for complete search history.

(56) References Cited

U.S. PATENT DOCUMENTS

| | | | |
|---|---|---|---|
| 4,073,014 A | 2/1978 | Poler | |
| 4,122,556 A | 10/1978 | Poler | |
| 4,575,373 A | 3/1986 | Johnson | |
| 4,661,108 A | 4/1987 | Grendahl et al. | |
| 4,919,151 A | 4/1990 | Grubbs et al. | |
| 5,026,783 A | 6/1991 | Grubbs et al. | |
| 5,074,942 A * | 12/1991 | Kearns et al. | 156/154 |
| 5,222,981 A | 6/1993 | Werblin | |
| 5,358,520 A | 10/1994 | Patel | |
| 5,480,426 A | 1/1996 | Chu | |
| 5,549,668 A | 8/1996 | O'Donnell, Jr. | |
| 5,571,177 A | 11/1996 | Deacon et al. | |
| 5,628,798 A | 5/1997 | Eggleston et al. | |
| 5,800,533 A | 9/1998 | Eggleston et al. | |
| 5,824,074 A * | 10/1998 | Koch | 623/6.34 |
| 5,922,821 A * | 7/1999 | LeBoeuf et al. | 526/286 |
| 6,015,842 A | 1/2000 | LeBoeuf et al. | |
| 6,406,494 B1 | 6/2002 | Laguette et al. | |
| 6,464,725 B2 | 10/2002 | Skotton | |
| 6,524,340 B2 * | 2/2003 | Israel | 623/6.44 |
| 6,797,004 B1 | 9/2004 | Brady et al. | |
| 2002/0173846 A1 | 11/2002 | Blake et al. | |
| 2003/0074061 A1* | 4/2003 | Pham et al. | 623/6.34 |
| 2003/0158560 A1 | 8/2003 | Portney | |
| 2003/0187504 A1 | 10/2003 | Weinschenk, III et al. | |

FOREIGN PATENT DOCUMENTS

WO    WO 01/87189    11/2001

* cited by examiner

*Primary Examiner*—William H. Matthews
(74) *Attorney, Agent, or Firm*—Jeffrey S. Schira

(57) ABSTRACT

A two or three component lens system. The first component is a ring-like supporting component that is implanted in the capsular bag following cataract surgery. The first component is a non-optical component and does not correct for any refractive errors. The first component may contains features to help reduce or eliminate PCO. The second component is an optical component that may contain all of the corrective optical power of the lens system. The second component has a pair of tabs for locking the second component within the first component. The third component is optional and is similar to second component and contains some optical power to correct for any residual optical error not corrected by the second component. The second and third components may also be implanted so as to move relative to one another, thereby providing some accommodation.

7 Claims, 4 Drawing Sheets

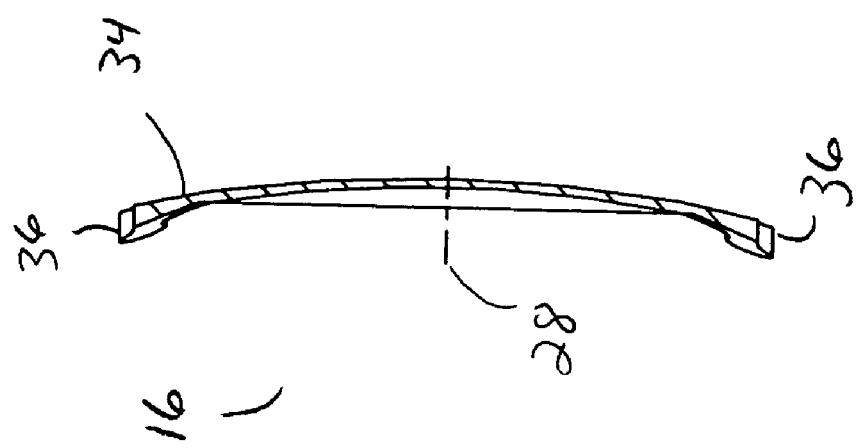
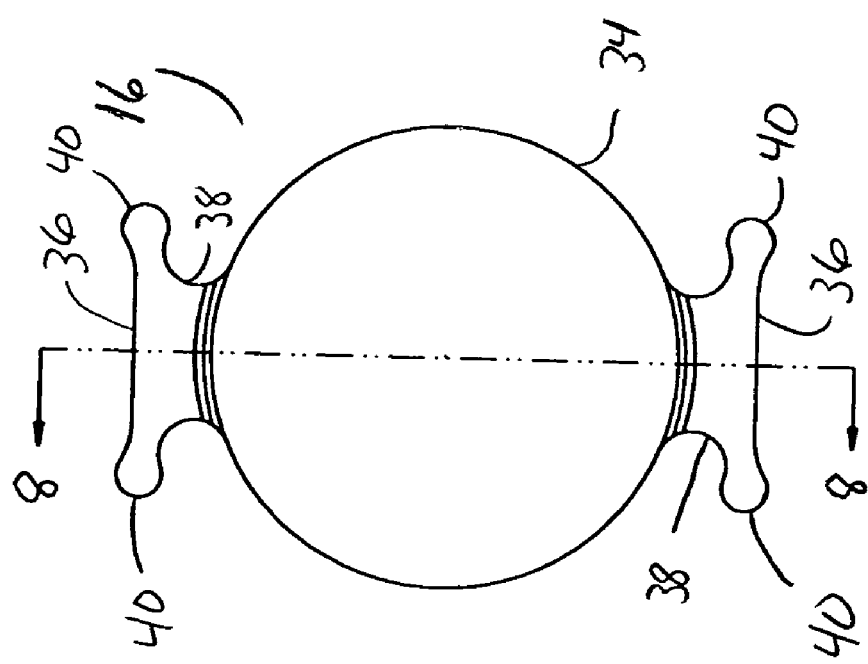
FIG. 8
FIG. 7

INTRAOCULAR LENS

BACKGROUND OF THE INVENTION

This invention relates generally to the field of intraocular lenses (IOL) and, more particularly, to multi-lens, micro-incision IOLs.

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Prior to the present invention, when a cataract or other disease required the removal of the natural lens and replacement with an artificial IOL, the IOL was a monofocal lens. Most IOLs are sold in power increments of +/−0.5 diopters, and the ultimate power of the lens depends upon where the lens sits along the optical axis. The fixed increment of the lens, and the slight variation in lens placement can result in less than optimum vision. Although this situation occurs relatively infrequently, and generally is not severe, some patients ultimately are required to use a pair of spectacles or contact lenses for optimum vision. If the power of the implanted lens is incorrect, removal and exchange of a new lens is difficult because of fibrosis of the lens haptics within the capsular bag.

There have been several prior suggested adjustable power IOLs, none of which have been commercially introduced. For example, U.S. Pat. No. 5,222,981 (Werblin) and U.S. Pat. No. 5,358,520 (Patel), the entire contents of which being incorporated herein by reference, suggest the use of a second or even a third optic that may be implanted and attached to a previously implanted primary optic so as to adjust the overall optic power of the multi-lens system. U.S. Pat. Nos. 5,628,798 and 5,800,533 (Eggleston, et al.), the entire contents of which being incorporated herein by reference, disclose a threadedly adjustable IOL wherein the location of the optic along the visual axis may be adjusted. U.S. Pat. No. 4,575,373 (Johnson), the entire contents of which being incorporated herein by reference, discloses an IOL having an optic and an outer ring and connections between the optic and the outer ring made from a heat-shrinkable plastic. The connections are heated with a laser to adjust the power of the IOL. U.S. Pat. Nos. 4,919,151 and 5,026,783 (Grubbs, et al.), the entire contents of which being incorporated herein by reference, disclose a lens made from a polymer that swells or otherwise changes shape. The lens is implanted or injected into the capsule bag and selectively polymerized so as to adjust the power of the optic. U.S. Pat. No. 5,571,177 (Deacon, et al.), the entire contents of which being incorporated herein by reference, discloses an IOL having haptics with frangible stiffeners. Once implanted in an eye, the stiffeners are selectively cut or heated above their $t_g$ by laser radiation, causing the stiffness of the haptic to change and adjusting the location of the lens within the capsule bag. The multi-lens designs and the threadedly adjustable designs are not optimized for the reduction or elimination of posterior capsule opacification (PCO). In addition, many of these lenses are not capable of being implanted through a vary small (less than 2 millimeters) incision.

Therefore, a need continues to exist for a safe and stable intraocular lens system that provides adjustment of lens power. Such a lens system could be used in cataract or clear lens exchange surgeries.

BRIEF SUMMARY OF THE INVENTION

The present invention improves upon the prior art by providing a two or three component lens system. The first component is a ring-like supporting component that is implanted in the capsular bag following cataract surgery. The first component is a non-optical component and does not correct for any refractive errors. The first component may contains features to help reduce or eliminate PCO. The second component is an optical component that may contain all of the corrective optical power of the lens system. The second component has a pair of tabs for locking the second component within the first component. The third component is optional and is similar to second component and contains some optical power to correct for any residual optical error not corrected by the second component. The second and third components may also be implanted so as to move relative to one another, thereby providing some accommodation.

Accordingly, one objective of the present invention is to provide a safe and biocompatible intraocular lens.

Another objective of the present invention is to provide a safe and biocompatible intraocular lens that is easily implanted in the posterior chamber.

Still another objective of the present invention is to provide a safe and biocompatible intraocular lens that is stable in the posterior chamber.

Still another objective of the present invention is to provide a safe and biocompatible adjustable lens system.

Still another objective of the present invention is to provide a safe and biocompatible lens system that can be implanted through a small incision.

Still another objective of the present invention is to provide a safe and biocompatible lens system that helps reduce the incidence of PCO.

Still another objective of the present invention is to provide a safe and biocompatible lens system for use in cataract and/or clear lens exchange surgeries.

These and other advantages and objectives of the present invention will become apparent from the detailed description and claims that follow.

BRIEF DESCRIPTION OF THE DRAWING

FIG. 7 is an enlarged plan view of the third component of the lens system of the present system.

FIG. 8 is an enlarged cross-sectional view of the third component of the lens system of the present system taken at line 8-8 in FIG. 7.

DETAILED DESCRIPTION OF THE INVENTION

Figure 1:
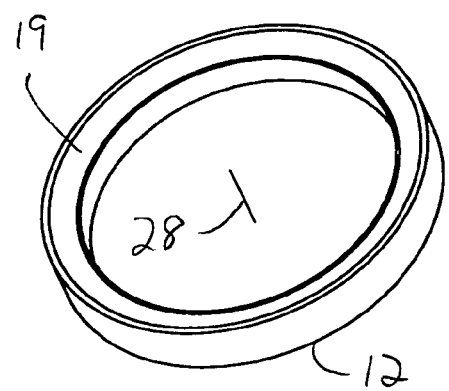
FIG. 1 is an enlarged perspective view of the first component of the lens system of the present system.
Figure 2:
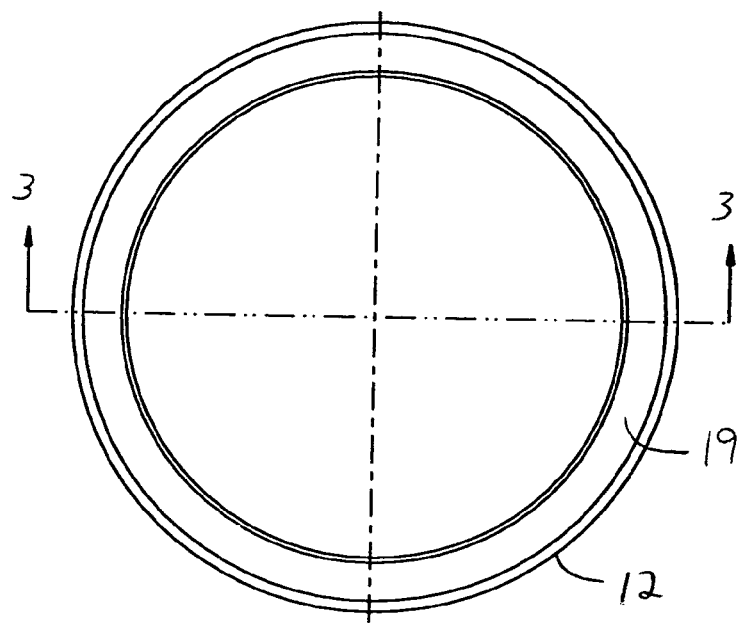
FIG. 2 is an enlarged plan view of the first component of the lens system of the present system.
Figure 3:
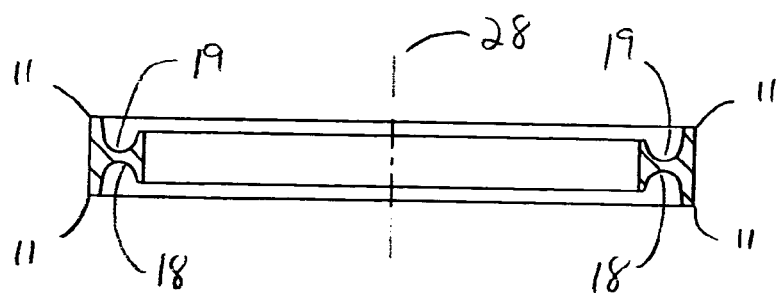
FIG. 3 is an enlarged cross-sectional view of the first component of the lens system of the present system taken at line 3-3 in FIG. 2.
Figure 4:
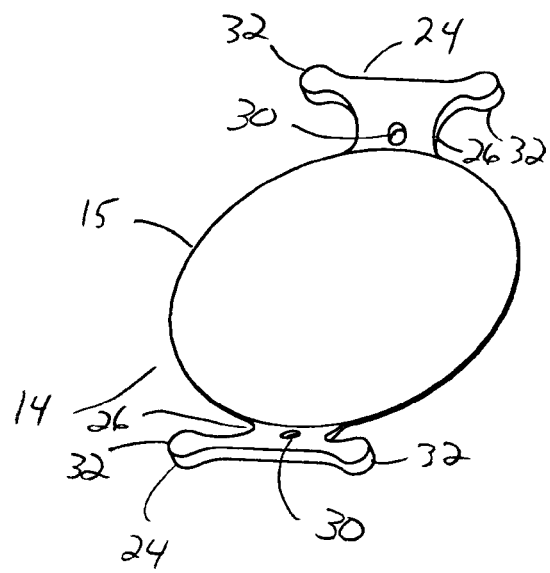
FIG. 4 is an enlarged perspective view of the second component of the lens system of the present system.

As best seen in FIGS. 1, 4 and 7, lens system 10 of the present invention generally includes a first, or base, component 12, second, or optical, component 14 and may optionally includes third, or secondary optical component 16. First component 12 is generally ring-like, and, as best seen in FIG. 3, is generally "I"-shaped in cross section. This "I"-shape forms circumferential anterior channel 19 and posterior channel 18 within the inner diameter of component 12. Such a construction is easy to mold, and provides the flexibility necessary to allow component 12 to be inserted into an eye through a sub-2 millimeter incision. Component 12 is constructed with sharp, square outer edges 11 to help prevent PCO. Component 12 is preferably formed in any suitable overall diameter, for example, between approximately 8.0 millimeters and 12.0 millimeters, a suitable interior diameter, for example, between approximately 6.0 millimeters and 8.5 millimeters and made from a soft, foldable material such as a soft acrylic. Alternatively, component 12 may be made from a material that is stiffer relative to optical component 14 or less stiff relative to optical component 14. By way of example, component 12 may be made of rubber elastomers, such as butyl rubber, latex rubber, natural rubber, pure gum rubber, neoprene rubber, acrylonitrile rubber, styrene-butadiene rubber, ethylene-propylene diene monomer rubber, acrylonitrile-butadiene-styrene (ABS) rubber, epichlorohydrin rubber, hypalon rubber, silicone rubber and siloxane elastomers, such as poly(dimethylsiloxane), polyurethane rubber, viton rubber, ethylene-butylene rubber, isobutylene rubber and elastomers of polyphosphazenes, like poly(bis-trifluorethoxyphosphazene) oly(dimethylphosphazene) and poly(phenylmethylphosphazene). Preferably, base component 12 may be formed so as to be opaque, such as by frosting or texturing the anterior and/or posterior surfaces of base component 12, or base component may be relatively clear. Base component 12 may also contain a chromophore to block ultraviolet and/or blue and/or green light, such chromophore(s) being well-known in the art.

Figure 5:
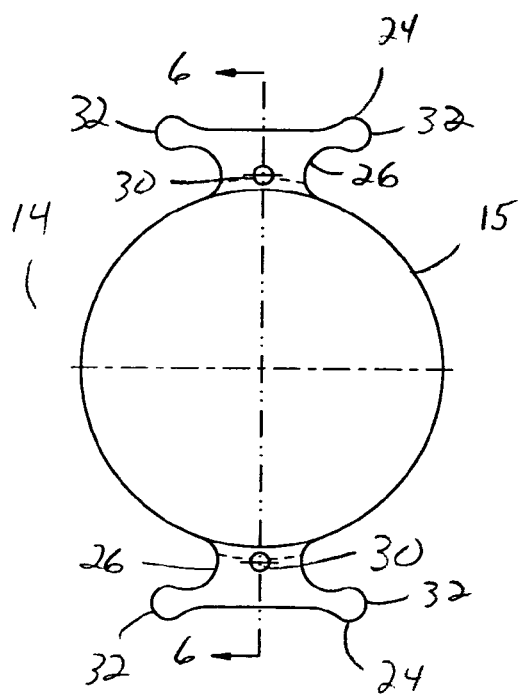
FIG. 5 is an enlarged plan view of the second component of the lens system of the present system.
Figure 6:
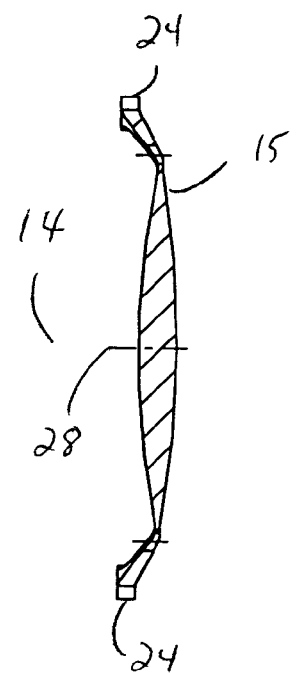
FIG. 6 is an enlarged cross-sectional view of the second component of the lens system of the present system taken at line 6-6 in FIG. 5.

As best seen in FIGS. 4-6, second component 14 is generally circular with an optic 15 having a diameter for example, between approximately 4.0 millimeters and 7.0 millimeters. Optic 15 tapers from being relatively thick in the middle to having a relatively thin, or sharp, edge that connects to a plurality of haptics 24 integrally formed with optic 15 so as to give optical component 14 overall length of between approximately 8.0 millimeters and 10.0 millimeters and preferably, is made from a soft, foldable material such as a soft acrylic. Second component 14 may also contain a chromophore to block ultraviolet and/or blue light, such chromophore(s) being well-known in the art, but unlike base component 12, second component 14 is optically clear. Haptics 24 are connected to optic 15 by connecting portions 26 that are relatively wide in plan view, but relatively thin in cross-section. In addition, haptics 24 contain outwardly projecting tips 32. Such a construction helps to prevent rotation of second component 14 within first component 12 and helps to maintain the stability of optical portion 14 in the plane perpendicular to optical axis 28, but allows some flexibility along optical axis 28. Connecting portions 26 may also contain positioning or manipulation holes 30.

As best seen in FIGS. 7-8, third component 16 is generally circular with an optic 34 having a diameter for example, between approximately 4.0 millimeters and 7.0 millimeters. Third component 16 contains a plurality of haptics 36 integrally formed with optic 34 so as to give third component 16 overall length of between approximately 8.0 millimeters and 10.0 millimeters and preferably, is made from a soft, foldable material such as a soft acrylic. Third component 16 may also contain a chromophore to block ultraviolet and/or blue light, such chromophore(s) being well-known in the art, but unlike base component 12, lens component 16 is optically clear. Haptics 36 are connected to optic 34 by connecting portions 38 that are relatively wide in plan view, but relatively thin in cross-section. In addition, haptics 36 contain outwardly projecting tips 40. Such a construction helps to prevent rotation of third component 16 within second component 12 and helps to maintain the stability of third component 16 in the plane perpendicular to optical axis 28, but allows some flexibility along optical axis 28. In general, third component 16 is of similar construction as second component 14 except, as best seen in FIGS. 6 and 8, third component 16 has less optical power than second component 14 and therefore, is generally thinner than second component 14. Either second component 14 or third component 16 may be constructed to correct any of a variety of possible refractive errors, such a astigmatism (toric), presbyopia (accommodative, pseudo-accommodative or multifocal) or customized to correct higher order aberrations, such refractive errors and optical corrections therefore being well-known in the art.

Figure 9:
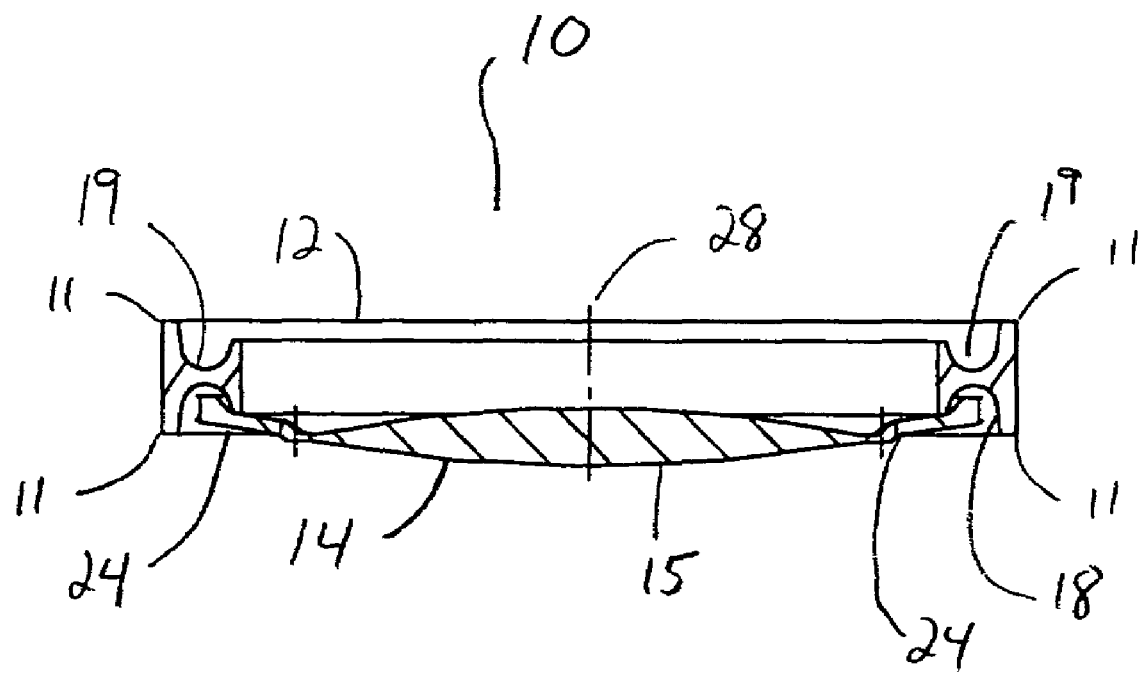
FIG. 9 is an enlarged cross-sectional view of the lens system of the present system with the second component installed within the first component.

As best seen in FIG. 9, lens system 10 is assembled by placing tips 32 or 40 of second component 14 or third component 16, respectively, into posterior channel 18 of first component 12, thereby compressing connecting portions 26 and 38 respectively and allowing both haptic 24 and 36 to snap within channel 18. Third component 16 may be installed in a similar manner to correct any residual refractive errors not corrected by second component 14. Preferably, third component 16 is rotated approximately 90° relative to second component 14.

This description is given for purposes of illustration and explanation. It will be apparent to those skilled in the relevant art that changes and modifications may be made to the invention described above without departing from its scope or spirit.

I claim:

1. An intraocular lens, comprising:
   a) a generally circular first component having an open center and a cross-sectional shape generally forming an open, anteriorly facing circumferential groove and an open, posteriorly facing circumferential groove the first component having a square outer edge; and
   b) a second component having an optical power, the second component having a plurality of haptics sized to fit within the posteriorly facing circumferential groove, wherein the first component and the second component are formed as separate components.

2. The lens of claim 1 wherein the first component is opaque.

3. The lens of claim 1 wherein the first component is stiff relative to the second component.

4. The lens of claim 1 wherein the first component is made from a rubber elastomer.

5. The lens of claim 1 wherein the second component contains a chromophore to block ultraviolet and/or blue and/or green light.

6. The lens of claim 1 wherein the first component is made from a soft acrylic.

7. The lens system of claim 4 wherein the first component is made from a material selected from the group consisting of butyl rubber, latex rubber, natural rubber, pure gum rubber, neoprene rubber, acrylonitrile rubber, styrene-butadiene rubber, ethylene-propylene diene monomer rubber, acrylonitrile-butadiene-styrene (ABS) rubber, epichlorohydrin rubber, hypalon rubber, silicone rubber and siloxane elastomers, isobutylene rubber and elastomers of polyphosphazenes.

* * * * *